United States Patent [19]

Urushibata et al.

[11] Patent Number: 5,536,837
[45] Date of Patent: Jul. 16, 1996

[54] N-SULFONYL CARBOXYLIC AMIDE DERIVATIVE

[75] Inventors: Ikumi Urushibata; Takumi Yoshimura; Takeshi Deguchi; Norihisa Yonekura; Junetsu Sakai; Shigeru Hayashi, all of Shizuoka-ken, Japan

[73] Assignees: Kumiai Chemical Industry Co., Ltd.; Ihara Chemical Industry Co., Ltd., both of Tokyo, Japan

[21] Appl. No.: 443,766

[22] Filed: May 18, 1995

Related U.S. Application Data

[62] Division of Ser. No. 137,190, filed as PCT/JP93/00273, Mar. 3, 1993, Pat. No. 5,444,060.

[30] Foreign Application Priority Data

Mar. 3, 1992 [JP] Japan ........................ 4-80264

[51] Int. Cl.$^6$ .................... C07D 239/26; C07D 403/12; A01N 43/54
[52] U.S. Cl. .................... 544/316; 544/229; 544/319; 544/312; 544/323; 544/327; 544/332; 544/334; 544/335; 540/601; 540/481
[58] Field of Search ................ 504/239, 219, 504/242, 243, 193; 544/229, 316, 312, 319, 323, 334, 327, 332, 335; 540/481, 601

[56] References Cited

PUBLICATIONS

Allen et al, Chemical Abstracts, vol. 116, entry 59392 (1991).
Ort et al, Chemical Abstracts, vol. 115, entry 183340 (1991).

*Primary Examiner*—John M. Ford
*Attorney, Agent, or Firm*—Oblon, Spivak, McClelland, Maier & Neustadt

[57] ABSTRACT

The present invention provides an N-sulfonyl carboxylic amide derivative including an N-containing 6-membered aromatic ring represented by formula [I]:

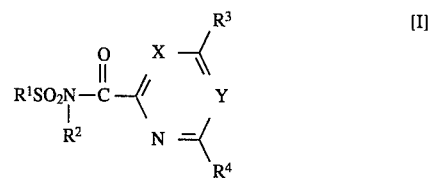

wherein $R^1$ represents an alkyl group, an alkenyl group, or the like, $R^2$ represents a hydrogen atom, an alkyl group, or the like, $R^3$ and $R^4$ represent independently an alkyl group, alkoxy group, or the like, and X and Y represent independently a methyne group or a nitrogen atom; or the salt of the same, a method for producing the same, and a biocide containing the same as an active ingredient. The N-sulfonyl carboxylic amide derivative including an N-containing 6-membered aromatic ring according to the present invention exhibits superior effects against blight caused by plant pathogenic fungi belonging to Oomycetes such as downy mildew, late blight, or the like in a low concentration as well as controls weeds occurring in paddy fields and plowed fields.

3 Claims, No Drawings

N-SULFONYL CARBOXYLIC AMIDE DERIVATIVE

This is a Division of application Ser. No. 08/137,190 filed on Nov. 2, 1993 now U.S. Pat. No. 5,444,060 which was filed as International Application No. PCT/JP93/00273 filed Mar. 3, 1993.

TITLE OF THE INVENTION

N-Sulfonyl carboxylic amide derivative

FIELD OF THE INVENTION

The present invention relates to an N-sulfonyl carboxylic amide derivatives including an N-containing 6-membered aromatic ring, or the salt of the same as well as a biocide containing the same as an active ingredient.

DISCUSSION OF THE BACKGROUND

Heretofore, some compounds possessing chemical structures similar to that of the N-sulfonyl carboxylic amide derivative according to the present invention have been known in Japanese Patent Application First Publication No. Hei 2-282371. The document discloses that such compounds possess effects as a plant growth modifier or as a herbicide.

DETAILED DESCRIPTION OF THE PREFERRED EMBODIMENTS

In agricultural production, blights caused by plant pathogenic fungi belonging to Oomycetes such as downy mildew, late blight, or the like occurs on many plants and this is one of the most difficult blights to control. For this reason, it is desired that an improved control agent be developed.

The present inventors have synthesized various N-sulfonyl carboxylic amide derivatives including N-containing 6-membered aromatic rings and have carried out extensive research in connection with their effects on the physiological activities of fungi. As a result, we have found that the N-sulfonyl carboxylic amide derivatives according to the present invention exhibit anti-fungal activity. The compounds which are active ingredients of a biocide according to the present invention are novel and can control various weeds occurring in paddy fields and plowed fields.

The present invention provides a biocide containing an N-sulfonyl carboxylic amide derivative including an N-containing 6-membered aromatic ring represented by formula [I]:

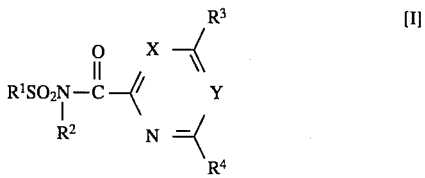

wherein $R^1$ represents an alkyl group x optionally having mono-substituent or poly-substituents selected from the group consisting of a halogen atom, a cycloalkyl group, an $R^7O$ group [wherein $R^7$ represents a hydrogen atom, an alkyl group, an alkenyl group, an alkynyl group, a phenyl group (optionally having mono-substituent or poly-substituents selected from the group consisting of a halogen atom, an alkyl group, an alkoxy group, a haloalkyl group, and an alkoxycarbonyl group)], an $R^7S(O)_n$ group (wherein $R^7$ has the same meaning as defined above, n is an integer from 0 to 2), an $R^7R^8N$ group [wherein $R^7$ has the same meaning as defined above, $R^8$ represents an alkyl group, an alkenyl group, an alkynyl group, an alkoxy group, an alkenyloxy group, alkynyloxy group, or a phenyl group (optionally having mono-substituent or poly-substituents selected from the group consisting of a halogen atom, an alkyl group, an alkoxy group, a haloalkyl group, and an alkoxycarbonyl group)], a trimethylsilyl group, a cyano group, an oxiranyl group, an $R^8CO$ group (wherein $R^8$ has the same meaning as defined above), and an $R^8C=NOR^9$ group (wherein $R^8$ has the same meaning as defined above, and $R^9$ represents an alkyl group, an alkenyl group, or an alkynyl group)}, an alkenyl group { optionally having mono-substituent or poly-substituents selected from the group consisting of a halogen atom, a phenyl group (optionally having mono-substituent or poly-substituents selected from the group consisting of a halogen atom, an alkyl group, an alkoxy group, a haloalkyl group, and an alkoxycarbonyl group)], a cycloalkyl group, an $R^7O$ group (wherein $R^7$ has the same meaning as defined above), an $R^7S(O)n$ group (wherein $R^7$ and n have the same meanings as defined above), an $R^7R^8N$ group (wherein $R^7$ and $R^8$ have the same meanings as defined above), a trimethylsilyl group, a cyano group, an $R^8CO$ group (wherein $R^8$ has the same meaning as defined above), and an $R^8C=NOR^9$ group (wherein $R^8$ and $R^9$ have the same meanings as defined above)}, an alkynyl group, a cycloalkyl group { optionally having mono-substituent or poly-substituents selected from the group consisting of a halogen atom, an alkyl group, a phenyl group (optionally having mono-substituent or poly-substituents selected from the group consisting of a halogen atom, an alkyl group, an alkoxy group, a haloalkyl group, and an alkoxycarbonyl group), an $R^7O$ group (wherein $R^7$ has the same meaning as defined above), an $R^7S(O)_n$ group (wherein $R^7$ and n have the same meanings as defined above), an $R^7R^8N$ group (wherein $R^7$ and $R^8$ have the same meanings as defined above), a trimethylsilyl group, a cyano group, an oxo group, a $=NOR^9$ group (wherein $R^9$ has the same meaning as defined above), an $R^8CO$ group (wherein $R^8$ has the same meaning as defined above), and an $R^8C=NOR^9$ group (wherein $R^8$ and $R^9$ have the same meanings as defined above)}, a cycloalkenyl group {optionally having mono-substituent or poly-substituents selected from the group consisting of a halogen atom, an alkyl group, a phenyl group (optionally having mono-substituent or poly-substituents selected from the group consisting of a halogen atom, an alkyl group, an alkoxy group, a haloalkyl group, and an alkoxycarbonyl group), an $R^7O$ group (wherein $R^7$ has the same meaning as defined above), an $R^7S(O)_n$ group (wherein $R^7$ and n have the same meanings as defined above), an $R^7R^8N$ group (wherein $R^7$ and $R^8$ have the same meanings as defined above), a trimethylsilyl group, a cyano group, an oxo group, a $=NOR^9$ group (wherein $R^9$ has the same meaning as defined above), an $R^8CO$ group (wherein $R^8$ has the same meaning as defined above), and an $R^8C=NOR^9$ group (wherein $R^8$ and $R^9$ have the same meanings as defined above)}, an $R^5R^6N$ group {wherein $R^5$ represents an alkyl group [optionally having mono-substituent or poly-substituents selected from the group consisting of a halogen atom, a cycloalkyl group, an $R^7O$ group (wherein $R^7$ has the same meaning as defined above), an $R^7S(O)_n$ group (wherein $R^7$ and n have the same meanings as defined above), an $R^7R^8N$ group (wherein $R^7$ and $R^8$ have the same meaning as defined above), a trimethylsilyl group, a cyano group, an oxiranyl group, an $R^8CO$ group (wherein $R^8$ has the same meaning as defined above), and an $R^8C=NOR^9$ group (wherein $R^8$ and $R^9$ have the same meanings as defined above)], an alkenyl group [optionally having mono-substituent or poly-substituents selected from the group consisting of a halogen atom, a phenyl group (optionally having mono-substituent or poly-substituents selected from the group consisting of a halogen atom, an alkyl group, an alkoxy group, a haloalkyl group, and an alkoxycarbonyl group), a cycloalkyl group, an $R^7O$ group (wherein $R^7$ has the same meaning as defined above), an $R^7S(O)_n$ group (wherein $R^7$ and n have the same meanings as defined above), an $R^7R^8N$ group (wherein $R^7$ and $R^8$ have the same meanings as defined above), a trimethylsilyl group, a cyano group, an $R^8CO$ group (wherein $R^8$ has the same meaning as defined above), and an $R^8C=NOR^9$ group (wherein $R^8$ and $R^9$ have the same meanings as defined above)], an alkynyl group, a cycloalkyl group [optionally having mono-substituent or poly-substituents selected from the group consisting of a halogen atom, an alkyl group, a phenyl group (optionally having mono-substituent or poly-substituents selected from the group consisting of a halogen atom, an alkyl group, an alkoxy group, a haloalkyl group, and an alkoxycarbonyl group), an $R^7O$ group (wherein $R^7$ has the same meaning as defined above), an $R^7S(O)_n$ group (wherein $R^7$ and n have the same meanings as defined above), an $R^7R^8N$ group (wherein $R^7$ and $R^8$ have the same meanings as defined above), a trimethylsilyl group, a cyano group, an oxo group, a $=NOR^9$ group (wherein $R^9$ has the same meaning as defined above), an $R^8CO$ group (wherein $R^8$ has the same meaning as defined above), and an $R^8C=NOR^9$ group (wherein $R^8$ and $R^9$ have the same meanings as defined above)], a cycloalkenyl group [optionally having mono-substituent or poly-substituents selected from the group consisting of a halogen atom, an alkyl group, a phenyl group (optionally having mono-substituent or poly-substituents selected from the group consisting of a halogen atom, an alkyl group, an alkoxy group, a haloalkyl group, and an alkoxycarbonyl group), an $R^7O$ group (wherein $R^7$ has the same meaning as defined above), an $R^7S(O)_n$ group (wherein $R^7$ and n have the same meanings as defined above), an $R^7R^8N$ group (wherein $R^7$ and $R^8$ have the same meanings as defined above), a trimethylsilyl group, a cyano group, an oxo group, a $=NOR^9$ group (wherein $R^9$ has the same meaning as defined above), an $R^8CO$ group (wherein $R^8$ has the same meaning as defined above), and an $R^8C=NOR^9$ group (wherein $R^8$ and $R^9$ have the same meanings as defined above)], an $R^7O$ group (wherein $R^7$ has the same meaning as defined above), and $R^6$ represents a hydrogen atom or $R^5$, $R^5$ and $R^6$ may be independent each other, or $R^5$ may form a 3-member ~ 8-member ring with $R^6$ and a nitrogen atom}, an $R^{10}CON(R^6)$ group {wherein $R^6$ has the same meaning as defined above, $R^{10}$ represents an alkyl group [optionally having mono-substituent or poly-substituents selected from the group consisting of a halogen atom, an $R^7O$ group (wherein $R^7$ has the same meaning as defined above), an $R^7S(O)_n$ group (wherein $R^7$ and n have the same meanings as defined above), an $R^7R^8N$ group (wherein $R^7$ and $R^8$ have the same meanings as defined above), and a cyano group], an alkenyl group [optionally having mono-substituent or poly-substituents selected from the group consisting of a halogen atom, an $R^7O$ group (wherein $R^7$ has the same meaning as defined above), an $R^7S(O)_n$ group (wherein $R^7$ and n have the same meanings as defined above), an $R^7R^8N$ group (wherein $R^7$ and $R^8$ have the same meanings as defined above), and a cyano group], a phenyl group (optionally having mono-substituent or poly-substituents selected from the group consisting of a halogen atom, an alkyl group, an alkoxy group, a haloalkyl group, and an alkoxycarbonyl group)}, or an $R^{10}SO_2N(R^6)$ group (wherein $R^6$ and $R^{10}$ have the same meanings as defined above), $R^2$ represents a hydrogen atom or an alkyl group (optionally having a substituent selected from the group consisting of an alkoxy group and an alkoxycarbonyl group), a benzyl group, or an alkenyl group, $R^3$ and $R^4$ represent independently a hydrogen atom, a halogen atom, an alkyl group, an $R^7O$ group (wherein $R^7$ has the same meaning as defined above), an $R^7S(O)_n$ group (wherein $R^7$ and n have the same meanings as defined above), an $R^7R^8N$ group (wherein $R^7$ and $R^8$ have the same meanings as defined above), a haloalkyl group, or a haloalkoxy group, X and Y represent independently a methyne group or a nitrogen atom, (with the proviso that X and Y do not represent a methylene group at the same time)], or the salt of the same as an active ingredient.

The N-sulfonyl carboxylic amide derivative including an N-containing 6-membered aromatic ring, represented by formula [I], can exist as geometrical isomers of E-configuration and Z-configuration. The present invention contains each geometrical isomer, and the mixture thereof in an arbitrary ratio. In the compound represented by formula [I], an "alkyl group" can be illustrated by an alkyl group possessing 1 to 10 carbon atoms, an "alkenyl group" can be illustrated by an alkenyl group possessing 2 to 8 carbon atoms, an "alkynyl group" can be illustrated by an alkynyl group possessing 2 to 8 carbon atoms, a "cycloalkyl group" can be illustrated by a cycloalkyl group possessing 3 to 8 carbon atoms, an "alkoxy group" can be illustrated by an alkoxy group possessing 1 to 6 carbon atoms, and a "halogen atom" can be illustrated by chlorine, bromine, fluorine, or iodine.

Next, the compounds according to the present invention are listed in Tables 1 and 2. The compound No. given in Tables 1 and 2 will be referred to in the subsequent description.

TABLE 1

| Compound No. | $R^1$ | $R^2$ | $R^3$ | $R^4$ | Physical Characteristics Melting Point (°C.) or Refractive Index ($n_D^{20}$) |
|---|---|---|---|---|---|
| 1 | $CH_3$ | H | $CH_3O$ | $CH_3O$ | 211–213 |
| 2 | $CF_3$ | H | $CH_3O$ | $CH_3O$ | 129–135 |
| 3 | $C_2H_5$ | H | $CH_3O$ | $CH_3O$ | 196–198 |
| 4 | $C_3H_7$ | H | $CH_3O$ | $CH_3O$ | 121–124 |
| 5 | $i\text{-}C_3H_7$ | H | $CH_3O$ | $CH_3O$ | 182–184 |
| 6 | $C_4H_9$ | H | $CH_3O$ | $CH_3O$ | 82–83 |
| 7 | $C_5H_{11}$ | H | $CH_3O$ | $CH_3O$ | 111–113 |
| 8 | $i\text{-}C_4H_9$ | H | $CH_3O$ | $CH_3O$ | 128–130 |
| 9 | $s\text{-}C_4H_9$ | H | $CH_3O$ | $CH_3O$ | 137–144 |
| 10 | $i\text{-}C_5H_{11}$ | H | $CH_3O$ | $CH_3O$ | 96–100 |
| 11 | $C_6H_{13}$ | H | $CH_3O$ | $CH_3O$ | 66–69 |
| 12 | $C_{10}H_{21}$ | H | $CH_3O$ | $CH_3O$ | 45–48 |
| 13 | $ClCH_2$ | H | $CH_3O$ | $CH_3O$ | 170–176 |
| 14 | $ClCH_2CH_2CH_2$ | H | $CH_3O$ | $CH_3O$ | 116–119 |
| 15 | 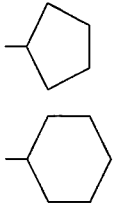 | H | $CH_3O$ | $CH_3O$ | 105–109 |
| 16 | 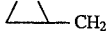 | H | $CH_3O$ | $CH_3O$ | 133–135 |
| 17 | $CH_2=CHCH_2$ | H | $CH_3O$ | $CH_3O$ | 118–120 |
| 18 | 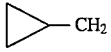 | H | $CH_3O$ | $CH_3O$ | 148–152 |
| 19 | $CH_2=C(CH_3)CH_2$ | H | $CH_3O$ | $CH_3O$ | 107–109 |
| 20 | $ClCH=CHCH_2$ | H | $CH_3O$ | $CH_3O$ | 104–106 |
| 21 | $(CH_3)_3CCH_2$ | H | $CH_3O$ | $CH_3O$ | 105–108 |
| 22 | 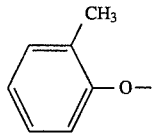 | H | $CH_3O$ | $CH_3O$ | 115–118 |
| 23 | $CH_2=C(Cl)CH_2$ | H | $CH_3O$ | $CH_3O$ | 125–130 |
| 24 | $ClCH=C(Cl)CH_2$ | H | $CH_3O$ | $CH_3O$ | 132–135 |
| 25 | $CH_2=CH$ | H | $CH_3O$ | $CH_3O$ | 186–189 |
| 26 | $CH_3OCOCH_2CH_2$ | H | $CH_3O$ | $CH_3O$ | 108–111 |
| 27 | $CH_3OCOCH_2$ | H | $CH_3O$ | $CH_3O$ | 95–98 |
| 28 | $CH_3$ | H | $CH_3O$ | $C_3H_7$ | 143–147 |
| 29 | $CH_3$ | H | $C_3H_7$ | $C_3H_7$ | 145–147 |
| 30 | $C_2H_5$ | H | $C_3H_7$ | $C_3H_7$ | 153–156 |
| 31 | $C_2H_5$ | H | $CH_3O$ | $C_3H_7$ | 170–174 |
| 32 | $C_3H_7$ | H | $C_3H_7$ | $C_3H_7$ | 93–97 |
| 33 | $C_4H_9$ | H | $C_3H_7$ | $C_3H_7$ | 70–76 |
| 34 | $C_3H_7$ | H | Cl | $(CH_3)_2N$ | 112–115 |
| 35 | $C_3H_7$ | H | $C_2H_5O$ | $C_2H_5O$ | 108–110 |
| 36 | $C_3H_7$ | H | $CH_3O$ | $CH_3$ | 98–102 |
| 37 | $C_3H_7$ | H | $CH_3O$ | $(CH_3)_2N$ | 134–137 |
| 38 | $i\text{-}C_4H_9$ | H | Cl | $(CH_3)_2N$ | 103–108 |
| 39 | $i\text{-}C_4H_9$ | H | $CH_3O$ | $CH_3$ | 1.5163 |
| 40 | $i\text{-}C_4H_9$ | H | $CH_3O$ | $(CH_3)_2N$ | |
| 41 | $i\text{-}C_4H_9$ | H | $CH_3O$ |  | 120–122 |

TABLE 1-continued $$R^1SO_2N(R^2)-C(=O)-\text{pyrimidine}(R^3, R^4)$$

| Compound No. | R¹ | R² | R³ | R⁴ | Physical Characteristics Melting Point (°C.) or Refractive Index ($n_D^{20}$) |
|---|---|---|---|---|---|
| 42 | $C_3H_7$ | H | $CH_3O$ | 2-methylphenoxy (o-CH₃-C₆H₄-O—) | 100–102 |
| 43 | i-$C_4H_9$ | H | $CH_3$ | $CH_3$ | 1.5169 |
| 44 | $(CH_3)_3CCH_2$ | H | $CH_3O$ | $C_2H_5O$ | 80–82 |
| 45 | s-$C_4H_9$ | $CH_3OCH_2$ | $CH_3O$ | $CH_3O$ | 1.5094 |
| 46 | $C_3H_7$ | $CH_3$ | $CH_3O$ | $CH_3O$ | 106–109 |
| 47 | $C_3H_7$ | $C_6H_5CH_2$— | $CH_3O$ | $CH_3O$ | 125–127 |
| 48 | $C_3H_7$ | $CH_3OCH_2$ | $CH_3O$ | $CH_3O$ | 59–62 |
| 49 | $C_3H_7$ | $C_2H_5OCOCH_2$ | $CH_3O$ | $CH_3O$ | 89–93 |
| 50 | $C_3H_7$ | $CH_2=CHCH_2$ | $CH_3O$ | $CH_3O$ | 128–132 |
| 51 | $C_3H_7$ | $C_2H_5OCOCH(CH_3)$ | $CH_3O$ | $CH_3O$ | 1.4733 |
| 52 | $CH\equiv CCH_2$ | H | $CH_3O$ | $CH_3O$ | 144–150 |
| 53 | $CH_3OCH_2CH_2$ | H | $CH_3O$ | $CH_3O$ | |
| 54 | $NCCH_2CH_2$ | H | $CH_3O$ | $CH_3O$ | 173–175 |
| 55 | $NCCH_2$ | H | $CH_3O$ | $CH_3O$ | |
| 56 | $CH_3CH_2CH(CH_3)CH_2$ | H | $CH_3O$ | $CH_3O$ | 107–110 |
| 57 | $C_6H_5$—$OCH_2CH_2$ | H | $CH_3O$ | $CH_3O$ | 90–92 |
| 58 | $C_6H_5$—$SCH_2$ | H | $CH_3O$ | $CH_3O$ | 99–100 |
| 59 | $C_6H_5$—$C(CH_3)_2$— | H | $CH_3O$ | $CH_3O$ | |
| 60 | $CH_3SCH_2$ | H | $CH_3O$ | $CH_3O$ | 125–126 |
| 61 | $C_6H_5$—$OCH_2$— | H | $CH_3O$ | $CH_3O$ | |
| 62 | $C_6H_5$—$COCH_2$— | H | $CH_3O$ | $CH_3O$ | 147–149 |

TABLE 1-continued $$R^1SO_2N-\underset{R^2}{\underset{|}{C}}-\underset{N}{\overset{O}{\overset{\|}{C}}}\underset{R^4}{\overset{R^3}{\underset{\|}{\diagdown}}}$$

| Compound No. | $R^1$ | $R^2$ | $R^3$ | $R^4$ | Physical Characteristics Melting Point (°C.) or Refractive Index ($n_D^{20}$) |
|---|---|---|---|---|---|
| 63 | $\underset{CH_3}{\overset{CH_3}{\diagdown}}C=CH-$ | H | $CH_3O$ | $CH_3O$ | |
| 64 | $\underset{Cl}{\overset{Cl}{\diagdown}}C=CH-$ | H | $CH_3O$ | $CH_3O$ | 125–128 |
| 65 | $CF_3CH_2-$ | H | $CH_3O$ | $CH_3O$ | 141–143 |
| 66 | $C_6H_5-CH=CH-$ | H | $CH_3O$ | $CH_3O$ | 173–176 |
| 67 | $HOCH_2CH_2$ | H | $CH_3O$ | $CH_3O$ | 101–105 |
| 68 | $C_6H_5-\underset{C-}{\overset{CH-CH_3}{\|}}$ | H | $CH_3O$ | $CH_3O$ | 120–122 |
| 69 | $\underset{CH_3}{\overset{CH_3}{\diagdown}}N-CH_2CH_2-$ | H | $CH_3O$ | $CH_3O$ | |
| 70 | $\underset{Na^+\ -O^-}{C_3H_7SO_2N=C}\underset{N}{\overset{N}{\diagdown}}\underset{OCH_3}{\overset{OCH_3}{\diagup}}$ | | | | 161–164 |
| 71 | $\left(\underset{O^-}{C_3H_7SO_2N=C}\underset{N}{\overset{N}{\diagdown}}\underset{OCH_3}{\overset{OCH_3}{\diagup}}\right)_2 Ca^{2+}$ | | | | 89–93 |
| 72 | $CH_3-\underset{Cl}{\overset{\|}{C}}=CHCH_2CH_2-$ | H | $CH_3O$ | $CH_3O$ | |
| 73 | $C_6H_5-CH=CHCH_2CH_2-$ | H | $CH_3O$ | $CH_3O$ | |
| 74 | $CH_3CH=CHCH_2CH_2-$ | H | $CH_3O$ | $CH_3O$ | |

TABLE 2

$$R^1SO_2N(R^2)-C(=O)-C(=N-C(R^3)=X)-... Y ...=N-C(R^4)$$

| Compound No. | R¹ | R² | R³ | R⁴ | X | Y | Physical Characteristics Melting Point (°C.) or Refractive Index ($n_D^{20}$) |
|---|---|---|---|---|---|---|---|
| 75 | BrCH₂— | H | CH₃O | CH₃O | N | CH | 165–168 |
| 76 | ClC(CH₃)=CHCH₂— | H | CH₃O | CH₃O | N | CH | 119–122 |
| 77 | CH₃CH=CHCH₂— (CH₃) | H | CH₃O | CH₃O | N | CH | 76–79 |
| 78 | ClCCH₂CH₂— (CH₃) | H | CH₃O | CH₃O | N | CH | 115–118 |
| 79 | BrCH₂CHCH₂— (Br) | H | CH₃O | CH₃O | N | CH | 113–115 |
| 80 | CH₂=C(CH₃)—CH₂CH₂— | H | CH₃O | CH₃O | N | CH | 94–96 |
| 81 | (C₂H₅)₂CHCH₂— | H | CH₃O | CH₃O | N | CH | 80–82 |
| 82 | C₃H₇CH(CH₃)— | H | CH₃O | CH₃O | N | CH | 124–125 |
| 83 | CH₃ON=C(C₆H₅)—CH₂— | H | CH₃O | CH₃O | N | CH | 136–139 |
| 84 | C₂H₅ON=C(C₆H₅)CH₂— | H | CH₃O | CH₃O | N | CH | 132–135 |
| 85 | Cl₂C=CHCH₂— | H | CH₃O | CH₃O | N | CH | 118–121 |
| 86 | C₂H₅OCO—CH(CH₃)— | H | CH₃O | CH₃O | N | CH | 119–121 |
| 87 | C₂H₅OCO—CH(C₂H₅)— | H | CH₃O | CH₃O | N | CH | 97–98 |
| 88 | CH₃SCH=CH— | H | CH₃O | CH₃O | N | CH | 129–132 |
| 89 | CH₃SCH₂CH₂— | H | CH₃O | CH₃O | N | CH | 117–118 |
| 90 | CF₃CF₂CF₂CF₂— | H | CH₃O | CH₃O | N | CH | 100–102 |
| 91 | CF₃CH₂CH₂— | H | CH₃O | CH₃O | N | CH | 147–149 |
| 92 | CF₂=CFCH₂CH₂— | H | CH₃O | CH₃O | N | CH | 100–106 |
| 93 | ClCH=C(CH₃)—CH₂— | H | CH₃O | CH₃O | N | CH | 101–105 |
| 94 | ClCH₂CH(CH₃)—CH₂— | H | CH₃O | CH₃O | N | CH | 1.5290 |

TABLE 2-continued $$R^1SO_2N(R^2)-C(=O)-C(=N-C(R^3)=Y-C(R^4)=N-)$$ (with X, Y in ring)

| Compound No. | $R^1$ | $R^2$ | $R^3$ | $R^4$ | X | Y | Physical Characteristics Melting Point (°C.) or Refractive Index ($n_D^{20}$) |
|---|---|---|---|---|---|---|---|
| 95 | $CH_2=C(Br)-CH_2-$ | H | $CH_3O$ | $CH_3O$ | N | CH | 105–106 |
| 96 | $CH_3CH=C(Cl)-CH_2-$ | H | $CH_3O$ | $CH_3O$ | N | CH | 128–129 |
| 97 | $BrCH=CHCH_2-$ | H | $CH_3O$ | $CH_3O$ | N | CH | 106–110 |
| 98 | $C_2H_5SCH_2-$ | H | $CH_3O$ | $CH_3O$ | N | CH | 120–121 |
| 99 | $i-C_3H_7-SCH_2-$ | H | $CH_3O$ | $CH_3O$ | N | CH | 107–108 |
| 100 | $CH_3SO_2CH_2-$ | H | $CH_3O$ | $CH_3O$ | N | CH | 218–220 |
| 101 | $C_2H_5SOCH_2-$ | H | $CH_3O$ | $CH_3O$ | N | CH | 154–157 |
| 102 | $C_2H_5SO_2CH_2-$ | H | $CH_3O$ | $CH_3O$ | N | CH | 173–178 |
| 103 | $(CH_3)_3Si-CH_2CH_2-$ | H | $CH_3O$ | $CH_3O$ | N | CH | 86–89 |
| 104 | $C_2H_5CH=CH-$ | H | $CH_3O$ | $CH_3O$ | N | CH | 98–102 |
| 105 | $(CH_3)_2N-$ | H | $CH_3O$ | $CH_3O$ | N | CH | 159–162 |
| 106 | $ClCH_2CH(Cl)-CH_2-$ | H | $CH_3O$ | $CH_3O$ | N | CH | 126–128 |
| 107 | $CH_2=C(C_6H_5)-CH_2-$ | H | $CH_3O$ | $CH_3O$ | N | CH | not determined |
| 108 | $i-C_3H_7-SO_2CH_2-$ | H | $CH_3O$ | $CH_3O$ | N | CH | 163–164 |
| 109 | $i-C_3H_7-SOCH_2-$ | H | $CH_3O$ | $CH_3O$ | N | CH | 175–176 |
| 110 | $C_2H_5OCOCH=CHCH_2-$ | H | $CH_3O$ | $CH_3O$ | N | CH | 127–129 |
| 111 | $(CH_2=CHCH_2)_2N-$ | H | $CH_3O$ | $CH_3O$ | N | CH | 74–76 |
| 112 | $C_6H_5-CH(CH_3)-$ | H | $CH_3O$ | $CH_3O$ | N | CH | 117–119 |
| 113 | $C_6H_5-CH(C_2H_5)-$ | H | $CH_3O$ | $CH_3O$ | N | CH | 149–151 |
| 114 | $C_6H_5-CH(C_3H_7)-$ | H | $CH_3O$ | $CH_3O$ | N | CH | 131–133 |
| 115 | $CH_2=CHCH(C_6H_5)-$ | H | $CH_3O$ | $CH_3O$ | N | CH | 134–135 |
| 116 | $(C_2H_5)_2N-$ | H | $CH_3O$ | $CH_3O$ | N | CH | 128–129 |

TABLE 2-continued $$R^1SO_2N(R^2)-C(=O)-C(=N-C(R^3)=Y-C(R^4)=N-)X$$

| Compound No. | $R^1$ | $R^2$ | $R^3$ | $R^4$ | X | Y | Physical Characteristics Melting Point (°C.) or Refractive Index ($n_D^{20}$) |
|---|---|---|---|---|---|---|---|
| 117 | $CH_2=CHCH_2CH(CH_3)-$ | H | $CH_3O$ | $CH_3O$ | N | CH | 90–91 |
| 118 | $i-C_3H_7-NH-$ | H | $CH_3O$ | $CH_3O$ | N | CH | 167–169 |
| 119 | $t-C_4H_9-NH-$ | H | $CH_3O$ | $CH_3O$ | N | CH | 216–219 |
| 120 | $CH_3CH=CH-$ | H | $CH_3O$ | $CH_3O$ | N | CH | 157–159 |
| 121 | $C_2H_5CH(CH_3)-NH-$ | H | $CH_3O$ | $CH_3O$ | N | CH | 154–156 |
| 122 | $CH_2=CHCH_2NH-$ | H | $CH_3O$ | $CH_3O$ | N | CH | 129–132 |
| 123 | $i-C_3H_7-CH_2NH-$ | H | $CH_3O$ | $CH_3O$ | N | CH | 118–119 |
| 124 | $CH_2=CHCH_2CH(OCOC_2H_5)-$ | H | $CH_3O$ | $CH_3O$ | N | CH | 79–80 |
| 125 | $CH_3NH-$ | H | $CH_3O$ | $CH_3O$ | N | CH | 233–234 |
| 126 | $C_2H_5NH-$ | H | $CH_3O$ | $CH_3O$ | N | CH | 190–193 |
| 127 | $C_3H_7NH-$ | H | $CH_3O$ | $CH_3O$ | N | CH | 123–124 |
| 128 | $C_4H_9NH-$ | H | $CH_3O$ | $CH_3O$ | N | CH | 119–121 |
| 129 | $CH\equiv CCH_2NH-$ | H | $CH_3O$ | $CH_3O$ | N | CH | 167–169 |
| 130 | $CH_3OCO-CH(C_3H_7-i)-$ | H | $CH_3O$ | $CH_3O$ | N | CH | 108–110 |
| 131 | $CH_3OCO-CH(C_3H_7)-$ | H | $CH_3O$ | $CH_3O$ | N | CH | 82–83 |
| 132 | cyclobutyl-$CH_2-$ | H | $CH_3O$ | $CH_3O$ | N | CH | 112–113 |
| 133 | cyclopentyl-$CH_2-$ | H | $CH_3O$ | $CH_3O$ | N | CH | 107–109 |
| 134 | cyclopentyl-$CH(COOCH_3)-$ | H | $CH_3O$ | $CH_3O$ | N | CH | 140–141 |
| 135 | cyclopropyl-$NH-$ | H | $CH_3O$ | $CH_3O$ | N | CH | 208–210 |
| 136 | pyrrolidin-1-yl | H | $CH_3O$ | $CH_3O$ | N | CH | 136–139 |
| 137 | 2-oxocyclopentyl | H | $CH_3O$ | $CH_3O$ | N | CH | 151–153 |

TABLE 2-continued $$R^1SO_2N(R^2)-C(=O)-C(=N-C(R^3)=Y-C(R^4)=N-)$$

| Compound No. | R¹ | R² | R³ | R⁴ | X | Y | Physical Characteristics Melting Point (°C.) or Refractive Index ($n_D^{20}$) |
|---|---|---|---|---|---|---|---|
| 138 | 2-oxocyclohexyl | H | CH₃O | CH₃O | N | CH | 121–122 |
| 139 | ClCH=C(Cl)—CH₂— | H | CH₃O | CH₃O | N | CH | 142–145 |
| 140 | CH₂=C(CH₃)—CH₂— | H | CH₃O | CH₃O | N | CH | 103–105 |
| 141 | ClCH=C(CH₃)—CH₂— | H | CH₃O | CH₃ | N | CH | 127–128 |
| 142 | ClCH=C(Cl)—CH₂— | H | CH₃ | CH₃ | N | CH | not determined |
| 143 | ClCH=C(Cl)—CH₂— | H | CH₃O | CH₃O | CH | N | 120–125 |
| 144 | CH₂=C(CH₃)—CH₂— | H | CH₃O | CH₃O | CH | N | 110–111 |
| 145 | ClCH=CHCH₂— | CH₃OCH₂ | CH₃O | CH₃O | N | CH | 92–96 |
| 146 | CH₂=C(CH₃)—CH₂— | CH₃OCH₂ | CH₃O | CH₃O | N | CH | 1.5128 |
| 147 | ClCH=C(Cl)—CH₂— | H | Cl | (CH₃)₂N— | N | CH | 164–170 |
| 148 | CH₂=C(CH₃)—CH₂— | H | Cl | (CH₃)₂N— | N | CH | 157–158 |
| 149 | ClCH=C(CH₃)—CH₂— | H | Cl | (CH₃)₂N— | N | CH | 148–151 |
| 150 | C₂H₅CH(CH₃)—CH₂— | H | Cl | (CH₃)₂N— | N | CH | 90–94 |
| 151 | ClCH=C(Cl)—CH₂— | H | CH₃O | (CH₃)₂N— | N | CH | 110–113 |
| 152 | CH₂=C(CH₃)—CH₂— | H | CH₃O | (CH₃)₂N— | N | CH | 125–127 |
| 153 | ClCH=C(CH₃)—CH₂— | H | CH₃O | (CH₃)₂N— | N | CH | 165–170 |
| 154 | 2-Cl-C₆H₄-SO₂N(CH₃)— | H | CH₃O | CH₃O | N | CH | 154–156 |
| 155 | 2-Cl-C₆H₄-CON(CH₃)— | H | CH₃O | CH₃O | N | CH | 142–143 |
| 156 | ClCH=CHCH₂— (Z) | H | CH₃O | CH₃O | N | CH | 162–163 |
| 157 | ClCH=CHCH₂— (E) | H | CH₃O | CH₃O | N | CH | 125–127 |
| 158 | CH₃ON(CH₃)— | H | CH₃O | CH₃O | N | CH | 144–145 |
| 159 | CH₃ONH— | H | CH₃O | CH₃O | N | CH | |
| 160 | C₂H₅ONH— | H | CH₃O | CH₃O | N | CH | |
| 161 | C₂H₅COCH(CH₃)— | H | CH₃O | CH₃O | N | CH | 179–180 |
| 162 | CH₃ON=C(C₂H₅)—CH(CH₃)— | H | CH₃O | CH₃O | N | CH | 88–90 |
| 163 | t-C₄H₉COCH₂— | H | CH₃O | CH₃O | N | CH | 84–86 |

TABLE 2-continued

Structure:
$$R^1SO_2N(R^2)-C(=O)-C(=N-C(R^3)=X)(-N=C(R^4)-Y)$$
(schematic with ring containing X, Y, and substituents $R^3$, $R^4$)

| Compound No. | $R^1$ | $R^2$ | $R^3$ | $R^4$ | X | Y | Physical Characteristics Melting Point (°C.) or Refractive Index ($n_D^{20}$) |
|---|---|---|---|---|---|---|---|
| 164 | (2-methylpiperidin-1-yl) | H | $CH_3O$ | $CH_3O$ | N | CH | 152–154 |
| 165 | $C_3H_7CH(CH_3)NH-$ | H | $CH_3O$ | $CH_3O$ | N | CH | 108–109 |
| 166 | $CH_3OCH_2CH(C_2H_5)NH-$ | H | $CH_3O$ | $CH_3O$ | N | CH | 142–144 |
| 167 | iso-$C_3H_7COCH_2-$ | H | $CH_3O$ | $CH_3O$ | N | CH | 104–107 |
| 168 | $CH_3SO_2N(CH_3)-$ | H | $CH_3O$ | $CH_3O$ | N | CH | 152–153 |
| 169 | $ClCH_2CH_2NH-$ | H | $CH_3O$ | $CH_3O$ | N | CH | 141–142 |
| 170 | (aziridin-1-yl) | H | $CH_3O$ | $CH_3O$ | N | CH | 131–134 |
| 171 | $CH_3CH=C(CH_3)CH_2-$ | H | $CH_3O$ | $CH_3O$ | N | CH | 106–108 |
| 172 | $C_2H_5CH=C(C_2H_5)-$ (E) | H | $CH_3O$ | $CH_3O$ | N | CH | 110–111 |

The compounds according to the present invention can be prepared by Preparation Processes A to E.

Preparation Process A (Scheme 1)

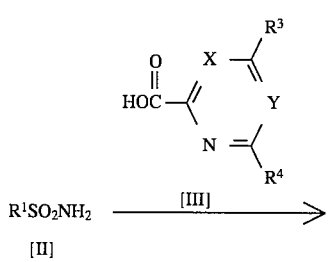

$R^1SO_2NH_2$    [III]  ⟶
[II]

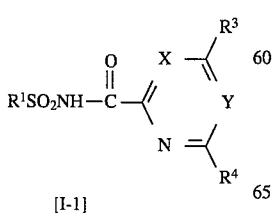

[I-1]

(wherein $R^1$, $R^3$, $R^4$, X and Y have the same meanings as defined above).

The compound represented by formula [I-1] can be prepared by reacting a compound represented by formula [II] with 1 ~ 1.5 equivalent of a compound represented by formula [III] in the presence of a condensing agent in a solvent.

As the condensing agent, there can be mentioned diethyl cyanophosphate, N, N'-carbonyldiimidazole, thionyl chloride, N,N'-dicyclohexylcarbodiimide, or the like.

As the solvent, there can be mentioned benzene, toluene, xylene, dichloromethane, chloroform, diethyl ether, tetrahydrofuran, dioxane, acetonitrile, N,N-dimethylformamide, N,N-dimethylacetamide, dimethylsulfoxide, or the like.

The reaction can be performed in a presence of a base such as triethylamine, sodium hydride, pyridine or the like, if necessary.

The present reaction can be carried out at an appropriate temperature of −20° C. to +50° C. for 30 minutes to 20 hours.

Preparation Process B (Scheme 2)

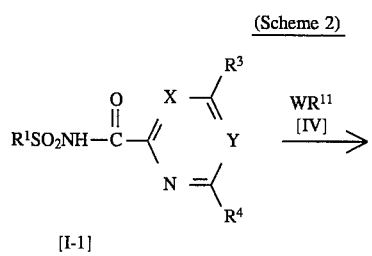

[wherein W represents a halogen atom, $R^1$, $R^3$, $R^4$, X and Y have the same meanings as defined above, $R^{11}$ represents an alkyl group (optionally being substituted with an alkoxy group or an alkoxycarbonyl group), a benzyl group, or an alkenyl group].

The compound represented by formula [I-2] can be prepared by reacting a compound represented by formula [I-1] with 1 ~ 1.5 equivalent of a compound represented by formula [IV] in the presence of a base in a solvent.

As the base, there can be mentioned triethylamine, sodium hydride, pyridine, or the like.

As the solvent, there can be mentioned benzene, toluene, xylene, diethyl ether, tetrahydrofuran, dioxane, acetonitrile, N,N-dimethylformamide, N,N-dimethylacetamide, dimethylsulfoxide, or the like.

The present reaction can be carried out at an appropriate temperature of −20° C. to +50° C. for 30 minutes to 20 hours.

Preparation Process C (Scheme 3)

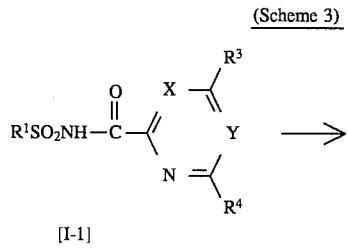

(wherein $M^+$ represents an alkaline metal, an alkaline earth metal, an ammonium, an organic ammonium, or a transition metal ion, and $R^1$, $R^3$, $R^4$, X, and Y have the same meanings as defined above).

The compound represented by formula [I-3] can be prepared by reacting a compound represented by formula [I-1] with 0.5 ~ 1 equivalent of a base in a solvent.

As the base, there can be mentioned an alkaline metal such as sodium, potassium, or the like, an alkaline metal hydride or an alkaline earth metal hydride such as sodium hydride, potassium hydride, calcium hydride or the like, an alkaline metal hydroxide or an alkaline earth metal hydroxide such as sodium hydroxide, potassium hydroxide, calcium hydroxide or the like, an alkaline metal alkoxide such as sodium methoxide, potassium t-butoxide, or the like, an organic amine such as ammonia, isopropylamine, or the like.

As the solvent, there can be mentioned benzene, toluene, xylene, diethyl ether, tetrahydrofuran, dioxane, acetonitrile, methanol, ethanol, N,N-dimethylacetamide, dimethylsulfoxide, water, or the like.

The present reaction can be carried out at an appropriate temperature of −20° C. to +50° C. for 30 minutes to 20 hours.

Preparation Process D (Scheme 4)

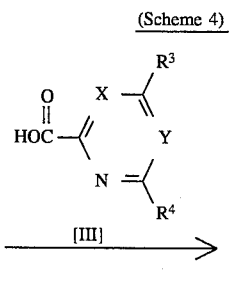

(wherein $R^1$, $R^3$, $R^4$, X and Y have the same meanings as defined above).

The compound represented by formula [I-1] can be prepared by reacting a compound represented by formula [VI] with 0.5 ~ 1 equivalent of a compound represented by formula [III] in a solvent.

As the solvent, there can be mentioned benzene, toluene, xylene, dichloromethane, chloroform, diethyl ether, tetrahydrofuran, dioxane, acetonitrile, N,N-dimethylformamide, N,N-dimethylacetamide, dimethylsulfoxide, or the like.

The reaction can be performed in the presence of a base such as triethylamine, sodium hydride, pyridine or the like, if necessary.

The present reaction can be carded out at an appropriate temperature of −20° C. to +50° C. for 30 minutes to 20 hours.

Preparation Process E (Scheme 5)

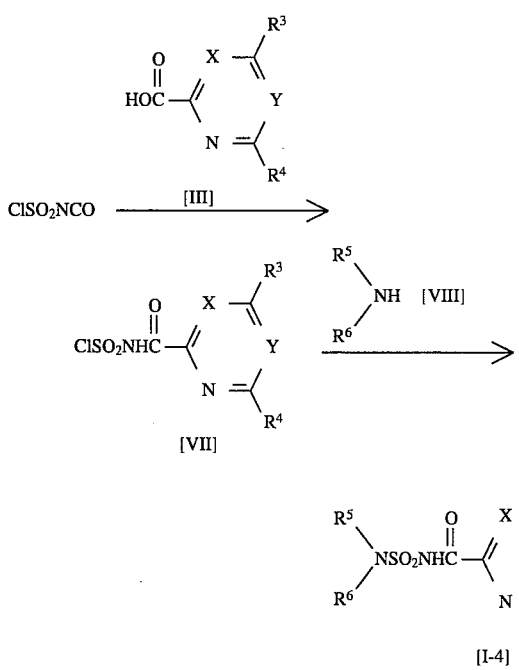

(wherein $R^3$, $R^4$, $R^5$, $R^6$, X, and Y have the same meanings as defined above).

The compound represented by formula [I-4] can be prepared by reacting a compound represented by formula [VII] with a compound represented by formula [VIII] in a solvent.

The reaction can be performed in the presence of a base such as triethylamine, sodium hydride, pyridine or the like, if necessary.

The compound represented by formula [VII] can be prepared by reacting a compound represented by formula [III] with 1 ~ 1.5 equivalent of chlorosulfonyl isocyanate in a solvent.

In either reaction mentioned above, as the solvent, there can be mentioned benzene, toluene, xylene, dichloromethane, chloroform, diethyl ether, tetrahydrofuran, dioxane, acetonitrile, dimethylsulfoxide, or the like. The present reaction can be carried out at an appropriate temperature of −20° C. to +50° C. for 30 minutes to 20 hours.

[Best mode for carrying out the invention]

The methods for producing the compounds according to the present invention will be described in detail in the following examples.

[Example 1]

Synthesis of N-isobutylsulfonyl-4,6-dimethoxypyrimidine-2-carboxylic amide (Compound No. 8)

1.8 g (11 mmol) of N,N-carbonyldiimidazole was added to a solution containing 2.0 g (11 mmol) of 4,6-dimethoxypyrimidine-2-carboxylic acid dissolved in 20 ml of N,N-dimethylformamide, and then the mixture was stirred for 1 hour at room temperature to prepare a solution containing 4,6-dimethoxypyrimidine-2-carbonylimidazole in N,N-dimethylformamide. Next, 0.5 g (12 mmol) of 60% sodium hydride was added to a solution containing 1.5 g (11 mmol) of isobutylsulfonamide dissolved in 20 ml of N,N-dimethylformamide. After the mixture was stirred for 1 hour at room temperature, the solution containing 4,6-dimethoxypyrimidine-2-carbonylimidazole in N,N-dimethylformamide was added thereto drop by drop at room temperature. After the reaction mixture was stirred for 3 hours at room temperature, the mixture was poured into cold water with ice. The pH of the mixture was adjusted by diluted hydrochloric acid to pH 2 ~ 3. The organic layer was extracted with 200 ml of ethyl acetate twice. The extract was washed with water, the organic layer was dried over anhydrous magnesium sulfate and then concentrated under reduced pressure to afford 3.1 g of a viscous liquid. The viscous liquid was purified by column chromatography on silica gel (ethyl acetate: hexane=1:1), thus obtaining 2.7 g of the desired product (yield 82.0%). White granular crystal, melting point: 128°–130° C.

[Example 2]

Synthesis of N-(2-chloro-2-propenylsulfonyl)-4,6-dimethoxypyrimidine-2-carboxylic amide (Compound No. 23)

2.4 g (13 mmol) of 4,6-dimethoxypyrimidine-2-carboxylic acid, 2.0 g (13 mmol) of 2-chloro-2-propenylsulfonamide, and 3.9 g (39 mmol) of triethylamine were dissolved in 50 ml of dichloromethane, and then the mixture was stirred for 30 minutes at room temperature. After 3.0 g (13 mmol) of 70% diethyl cyanophosphate was added to the mixture, the whole mixture was stirred at room temperature overnight. The reaction mixture was washed with diluted hydrochloric acid to remove the excess of triethylamine, and subsequently the product was extracted with 50 ml of a saturated aqueous solution of sodium bicarbonate. The extract was acidified by diluted hydrochloric acid to possess pH 2 ~ 3. The organic layer was extracted by 200 ml of ethyl acetate twice. The extract was washed with water, the organic layer was dried over anhydrous magnesium sulfate and then concentrated under reduced pressure to afford 1.8 g of a viscous liquid. The viscous liquid was purified by column chromatography on silica gel (ethyl acetate: hexane=1:1), thus obtaining 1.4 g of the desired product (yield 33.7%). Yellow powder, melting point: 125°–130° C.

[Example 3]

Synthesis of 4,6-dimethoxy-N-methoxymethyl-N-propylsulfonylpyrimidine-2-carboxylic amide (Compound No. 48)

0.32 g (8.0 mmol) of sodium hydride in limited amounts was added to a solution containing 2.0 g (6.8 mmol) of 4,6-dimethoxy-N-propylsulfonylpyrimidine-2-carboxylic acid dissolved in 100 ml of N,N-dimethylformamide, and then the mixture was stirred for 1 hour at room temperature. After 0.54 g (6.8 mmol) of methoxymethylchloride was added to the mixture, the whole mixture was stirred at room temperature for 1 hour. The reaction mixture was poured into water. The organic layer was extracted with toluene and dried over anhydrous magnesium sulfate and then concentrated under reduced pressure to afford a crude product containing 4,6-dimethoxy-N-methoxymethyl-N-propylsulfonylpyrimidine-2-carboxylic amide. The crude product was purified by column chromatography on silica gel (ethyl acetate:hexane=1:1), thus obtaining 0.5 g of the desired product (yield 22.1%). White powder, melting point: 59°–62° C.

[Example 4]

Synthesis of 4,6-dimethoxy-N-propylsulfonylpyrimidine-2-carboxylic amide sodium salt (Compound No. 70)

0.7 g (3.6 mmol) of 28% sodium methoxide was added to a solution containing 1.0 g (3.5 mmol) of 4,6-dimethoxy- N-propylsulfonylpyrimidine-2-carboxylic acid dissolved in 20 ml of methanol, and then the mixture was stirred for 1 hour at room temperature. The reaction mixture was concentrated. Ether was added to the obtained residue. Crystals were filtrated, washed with ether, and then dried, thus obtaining 0.9 g of the desired product. White powder, melting point: 161°–164° C.

[Example 5]

Synthesis of 4,6-dimethoxy-N-butylsulfonylpyrimidine-2-carboxylic amide (Compound No. 6)

3.0 g (16 mmol) of 4,6-dimethoxypyrimidine-2-carboxylic acid, 2.6 g (16 mmol) of butylsulfonylisocyanate, and 1.8 g (16 mmol) of triethylamine were dissolved in 200 ml of chloroform, and then the mixture was stirred for 6 hours at room temperature. After the reaction mixture was washed with 10% hydrochloric acid and water, the organic layer was dried over anhydrous magnesium sulfate and then concentrated under reduced pressure to afford a crude product containing 4,6-dimethoxy-N-butylsulfonylpyrimidine-2-carboxylic amide. The crude product was purified by column chromatography on silica gel (ethyl acetate:hexane=1:1), thus obtaining 1.5 g of the desired product (yield 30.3%). White powder, melting point: 82°–83° C.

[Example 6]

Synthesis of 4,6-dimethoxy-N-(isopropylaminosulfonyl)pyrimidine-2-carboxylic amide (Compound No. 118)

2.8 g (20 mmol) of chlorosulfonylisocyanate in limited amounts was added to a solution containing 3.0 g (16 mmol) of 4,6-dimethoxypyrimidine-2-carboxylic acid dissolved in 100 ml of dichloromethane, and then the mixture was stirred for 1 hour at room temperature. After 3.0 g (50 mmol) of isopropylamine was added to the reaction mixture drop by drop at room temperature, the mixture was stirred at room temperature for 3 hour. The reaction mixture was washed with 10% hydrochloric acid and water. The organic layer was dried over anhydrous magnesium sulfate and then concentrated under reduced pressure to afford a crude product containing 4,6-dimethoxy-N-(isopropylaminosulfonyl)pyrimidine-2-carboxylic amide. The crude product was purified by column chromatography on silica gel (ethyl acetate:hexane=1:3), thus obtaining 0.8 g of the desired product (yield 16.0%). White powder, melting point: 167°–169° C.

The biocide according to the present invention is a composition containing an N-sulfonyl carboxylic amide derivative including an N-containing 6-membered aromatic ring represented by formula [I] as an active ingredient. In the case where the compounds according to the present invention are employed as a biocide, the compounds acting as the active ingredient can be formulated appropriately, depending on the purpose. The active ingredient is usually diluted in an inert liquid or a solid carrier, and a surfactant, a dispersant, an adjuvant, and the like are added thereto if necessary. The mixture is then formulated into a fine powder, a wettable powder, an emulsifiable concentrate, granules, or the like.

As a suitable carrier employed in the formulation, there can be mentioned, for example, solid careers such as talc, bentonite, clay, kaolin, diatomaceous earth, white carbon, vermiculite, slaked lime, siliceous sand, ammonium sulfate, urea, or the like; and liquid careers such as isopropyl alcohol, xylene, cyclohexanone, methylnaphthalene, and the like. Illustrative examples of the surfactants and dispersants include salts of dinaphthylmethanesulfonic acid, alkylarylsulfonic acid, and lignosulfonic acid, sulfate esters of alcohol, polyoxyethylene glycol ethers, polyoxyethylene alkyl aryl ethers, polyoxyethylenesorbitan monoalkylates, and the like. Suitable examples of auxiliary agents include carboxymethylcellulose and the like. These preparations can be applied directly, or after diluting the preparation to a suitable concentration.

The biocide according to the present invention can be employed for spraying of stem and leaf portions, injection into irrigation water, or soil application. The proportion of the active ingredient is selected as needed. When formulated into a fine powder or granules, 0.1% by weight to 20% by weight of the active ingredient is preferred. For an emulsifiable concentrate or wettable powder, 5% by weight to 80% by weight of the active ingredient is adequate.

The rate of application of the biocide according to the present invention may vary depending on the type of active compound employed, the kind of the pest or disease to be controlled, the nature of occurrence of the pest or disease, the degree of damage, environmental conditions, the form of preparation to be used, and the like. When the biocide of the present invention is applied directly in the form of fine powder or granules, it is recommended that the rate of application of the active ingredient be suitably chosen within the range of 0.1 g to 5 kg per 10 ares, preferably, in the range of 1 g to 1 kg per 10 ares. In addition, when the biocide of the present invention is in the form of a liquid such as an emulsifiable concentrate or a wettable powder, it is recommended that the ratio for application of the active ingredient be suitably chosen within the range of 0.1 ppm to 10,000 ppm, and preferably within the range of 10 ppm to 3,000 ppm.

The biocides according to the present invention formulated in the formulation described above can control plant diseases caused by fungi belonging to Oomycetes. The fungi include, but are not limited to, Pseudoperonospora such as cucumber downy mildew (*Pseudoperonospora cubensis*), Plasmopara such as grape downy mildew (*Plasmopara viacola*), and Phytophthora such as tomato late blight (*Phytophthora infestans*).

The biocide according to the present invention may be employed in combination with fungicides, insecticides, herbicides, plant growth modifiers, fertilizers or the like, if necessary.

Next, the representative formulations are illustrated with reference to the following Formulation Examples, wherein all "%" represent "percent by weight".

[Formulation Example 1]

Fine powder

2% of Compound (93), 5% of diatomaceous earth, and 93% of clay were uniformly mixed and ground into a fine powder.

[Formulation Example 2]

Wettable powder

50% of Compound (95), 45% of diatomaceous earth, 2% of sodium dinaphthylmethanesulfonate, and 3% of sodium lignosulfonate were uniformly mixed and ground into a wettable powder.

[Formulation Example 3]

Emulsifiable concentrate

30% of Compound (80), 20% of cyclohexanone, 11% of polyoxyethylene alkylaryl ether, 4% of calcium alkylbenzenesulfonate, and 35% of methylnaphthalene were uniformly dissolved, thus obtaining an emulsifiable concentrate.

[Formulation Example 4]

Granules

5% of Compound (98), 2% of sodium lauryl sulfonate, 5% of sodium lignosulfonate, 2% of carboxymethylcellulose, and 86% of clay were uniformly mixed and ground. 20% of water was added to the ground mixture. The resulting mixture was kneaded and formed into granules of 14 mesh to 32 mesh by means of an extrusion granulator, and then dried into the desired granules.

The biocide according to the present invention can be employed as a herbicide in order to control harmful weeds. In this case, with regard to the formulation, the use, or the like, it is preferable that the biocide be used under the best conditions for use as a herbicide. However, even under the conditions for the biocide described above, the biocide according to the present invention can achieve the purposes of the herbicide.

[Effect of the invention]

The N-sulfonyl carboxylic amide derivatives including an N-containing 6-membered aromatic ring according to the present invention not only exhibit superior ability to prevent fungal infection, but also exhibit superior ability to eliminate pathogenic fungi, after it has invaded a host plant, in a low concentration, of a plant pathogenic disease belonging to Oomycetes, especially against downy mildew and late blight, compared with the conventional compounds disclosed in Japanese Patent Application First Publication No. Hei 2-282371. In addition, the biocides according to the present invention are also characterized in that they exhibit excellent characteristics such as residual activity and resistance to rain-fall on effectiveness.

Furthermore, the compounds according to the present invention can also control weeds occurring in paddy fields or plowed fields. The compounds exhibit superior effects against various weeds in plowed fields including broad leaf weeds such as duck-leaved, slender amaranth, common lambsquarters, blue morningglory, common cucklebur, and the like, as well as perenial and annual cyperaceous weeds such as purple nutsedge, yellow nutsedge, himekugu (*cyperus brevifolius*), sege weed, rice flatsedge, and the like, and gramineous weeds such as barnyardgrass, johnsongrass, blackgrass, and the like, from their germination stage to their growth stage. In addition, the compounds can also control annual weeds in paddy fields such as early watergrass, smallflower, duck-tongue weed, and the like, as well as perenial weeds such as Japanese ribbon wapato, water nutgrass, water chestnut, Japanese bulrush, narrow-leaved arrowhead, and the like.

As a suitable product, there can be mentioned rice plant, common field products, fruit trees, and the like.

The effects of the biocides according to the present invention will now be illustrated with reference to the following Test Examples.

Test Example 1:

Test on the Effectiveness in Preventing Infection by Cucumber Downy Mildew (*Pseudoperonospora cubensis*)

Cucumber seeds (variety: "Sagami hanjiro") were sown at a rate of 12 seeds each in a square PVC (polyvinyl chloride) pot, wherein each side was 9 cm wide. The seeds were allowed to grow in a greenhouse, for 7 days, to the cotyledonous stage. A wettable powder prepared as in Formulation Example 2 was diluted with water to a concentration of 500 ppm of the active ingredient, and the aqueous preparation obtained was then applied at a rate of 10 ml per pot to the cucumber seedlings in the cotyledonous stage. After drying in the air, the plant was inoculated with a spore suspension of cucumber downy mildew (*Pseudoperonospora cubensis*) fungi and then placed in a moist chamber at 22° C. for 24 hours, and then placed in a greenhouse. On the seventh day after the inoculation, the extent of lesions was rated in accordance with the following standards of evaluation in order to confirm the preventive effects of the compounds according to the present invention. The results of the test are given in Table 3.

For comparison, the following compounds disclosed in Japanese Patent Application First Publication No. Hei 2-282371 were employed.

Comparative Compound A:

N-(2-chlorophenylsulfonyl)-4,6-dimethoxypyrimidine-2-carboxylic amide

Comparative Compound B:

N-(2,6-dichlorophenylsulfonyl)-4,6-dimethoxypyrimidine-2-carboxylic amide

Standards of Evaluation:

Class A: No lesions were observed.

Class B: Incidence area less than 25%.

Class C: Incidence area 25% or more and less than 50%.

Class D: Incidence area 50% or more.

TABLE 3

| Compound No. | Preventive Effect Evaluation |
|---|---|
| 3 | A |
| 4 | A |
| 5 | A |
| 6 | A |
| 8 | A |
| 9 | B |
| 14 | A |
| 17 | A |
| 18 | A |
| 19 | A |
| 20 | A |
| 22 | A |
| 23 | A |
| 24 | A |
| 48 | B |
| 77 | A |
| 78 | B |
| 79 | A |
| 81 | A |
| 93 | A |
| 94 | A |
| 95 | A |
| 96 | A |
| 98 | A |
| 104 | A |
| 105 | B |
| 106 | B |
| 116 | A |
| 120 | A |
| 121 | B |
| 129 | A |
| 132 | B |
| 135 | A |
| 139 | A |
| 145 | A |
| 147 | B |
| 151 | A |
| 152 | A |
| 153 | A |
| Comparative Compound A | D |
| Comparative Compound B | D |

Test Example 2:

Test on the Effectiveness in Treating Infection by Cucumber Downy Mildew (*Pseudoperonospora cubensis*)

Cucumber seeds (variety: "Sagami hanjiro") were sown at a rate of 12 seeds each in a square PVC (polyvinyl chloride) pot, wherein each side was 9 cm wide. The seeds were allowed to grow in a greenhouse, for 7 days, to the cotyledonous stage. The seedlings were inoculated by spraying a zoosporangium suspension of cucumber downy mildew (*Pseudoperonospora cubensis*) fungi and then placed in a moist chamber at 22° C. for 24 hours. After drying in the air, a wettable powder prepared as in Formulation Example 2 was diluted with water to a concentration of 500 ppm of the active ingredient, and the aqueous preparation obtained was then applied at a rate of 10 ml per pot to the cucumber seedlings. The seedlings were then placed in a greenhouse. On the seventh day after the inoculation, the extent of lesions was rated in accordance with the standards of evaluation as disclosed in Test Example 1 in order to confirm the effect of treating the infection with the compounds according to the present invention. The results of the test are given in Table 4.

TABLE 4

| Compound No. | Treatment Effect Evaluation |
|---|---|
| 3 | B |
| 4 | B |
| 5 | A |
| 6 | A |
| 8 | B |
| 9 | B |
| 14 | A |
| 17 | A |
| 18 | A |
| 19 | A |
| 20 | A |
| 22 | A |
| 23 | B |
| 24 | B |
| 48 | B |
| 79 | A |
| 93 | B |
| 94 | B |
| 95 | A |
| 96 | B |
| 98 | B |
| 145 | A |

Test Example 3:

Test on Herbicidal Effectiveness by Paddy Field Soil Treatment

In a plastic pot (100 cm$^2$) filled with paddy field soil, seeds of early watergrass (abbreviated to as "Eo"), duck-tongue weed (abbreviated to as "Mo"), and Japanese bulrush (abbreviated to as "Sc") were sown, and covered with water to a depth of 3 cm. The next day, a wettable powder prepared in accordance with Formulation Example 2 was diluted with water and applied to the paddy field soil with water at a rate of 100 g of the active ingredient per 10 ares, followed by growing in a greenhouse. The herbicidal evaluation was conducted on the 21st day after treatment. The results were evaluated in accordance with the standards as identified in Table 5 and shown by the index numbers in Table 6.

As comparative agents, the same comparative compounds as disclosed in Test Example 1 were employed.

TABLE 5

| Incidence Index No. | Herbicidal Effects and Phytotoxicity (Control Degree of Growth) |
|---|---|
| 5 | 90% or more of herbicidal effects and phytotoxicity |
| 4 | 70% or more and less than 90% of herbicidal effects and phytotoxicity |
| 3 | 50% or more and less than 70% of herbicidal effects and phytotoxicity |
| 2 | 30% or more and less than 50% of herbicidal effects and phytotoxicity |
| 1 | 10% or more and less than 30% of herbicidal effects and phytotoxicity |
| 0 | less than 10% of herbicidal effects and phytotoxicity |

TABLE 6

| Compound No. | Herbicidal Effects | | |
|---|---|---|---|
| | Eo | Mo | Sc |
| 3 | 5 | 5 | 5 |
| 4 | 5 | 5 | 5 |
| 5 | 5 | 5 | 5 |
| 6 | 5 | 5 | 5 |
| 8 | 5 | 5 | 5 |
| 9 | 5 | 5 | 5 |
| 14 | 4 | 5 | 5 |
| 15 | 5 | 5 | 5 |
| 17 | 5 | 5 | 5 |
| 18 | 5 | 5 | 5 |
| 19 | 5 | 5 | 5 |
| 20 | 5 | 5 | 5 |
| 21 | 5 | 5 | 5 |
| 22 | 5 | 5 | 5 |
| 23 | 5 | 5 | 5 |
| 24 | 5 | 5 | 5 |
| 38 | 5 | 5 | 3 |
| 39 | 5 | 5 | 5 |
| 40 | 5 | 5 | 3 |
| 43 | 5 | 5 | 3 |
| 44 | 5 | 5 | 5 |
| 45 | 5 | 5 | 5 |
| 48 | 5 | 5 | 5 |
| 52 | 5 | 5 | 5 |
| 56 | 5 | 5 | 5 |
| 77 | 5 | 5 | 5 |
| 79 | 5 | 5 | 5 |
| 80 | 5 | 5 | 5 |
| 81 | 5 | 5 | 5 |
| 82 | 5 | 5 | 4 |
| 85 | 5 | 5 | 4 |
| 93 | 5 | 5 | 5 |
| 94 | 5 | 5 | 5 |
| 95 | 5 | 5 | 5 |
| 96 | 5 | 5 | 5 |
| 97 | 5 | 5 | 5 |
| 98 | 5 | 5 | 5 |
| 101 | 5 | 5 | 4 |
| 104 | 5 | 5 | 5 |
| 106 | 5 | 5 | 5 |
| 118 | 5 | 5 | 5 |
| 119 | 5 | 5 | 5 |
| 120 | 5 | 5 | 5 |
| 121 | 5 | 5 | 5 |
| 122 | 5 | 5 | 5 |
| 132 | 5 | 5 | 5 |
| 134 | 5 | 5 | 3 |
| 139 | 5 | 5 | 5 |
| 140 | 5 | 5 | 5 |
| 141 | 5 | 5 | 5 |
| 142 | 5 | 5 | 5 |
| 145 | 5 | 5 | 5 |

TABLE 6-continued

| Compound No. | Herbicidal Effects | | |
|---|---|---|---|
| | Eo | Mo | Sc |
| 146 | 5 | 5 | 5 |
| 147 | 5 | 5 | 5 |
| 148 | 5 | 5 | 5 |
| 149 | 5 | 5 | 3 |
| 150 | 5 | 5 | 3 |
| 151 | 5 | 5 | 5 |
| 152 | 5 | 5 | 5 |
| 153 | 5 | 5 | 5 |
| 156 | 5 | 5 | 5 |
| Comparative Example A | 1 | 3 | 1 |
| Comparative Example B | 1 | 3 | 1 |

Test Example 4:

Test on Herbicidal Effectiveness by Plowed Field Soil Treatment

In a plastic pot (120 cm$^2$) filled with plowed field soil, seeds of barnyardgrass (abbreviated to as "Ec"), duckleaved (abbreviated to as "Po"), slender amaranth (abbreviated to as "Am"), common lambsquarters (abbreviated to as "Ch"), and rice flatsedge (abbreviated to as "Ci") were sown, and covered with soil. A wettable powder prepared in accordance with Formulation Example 2 was diluted with water and sprayed uniformly on the surface of the plowed field soil using a compact sprayer at a rate of 100 L of the wettable powder per 10 ares so that the ratio of the active ingredient was 400 g per 10 ares, followed by growing in a greenhouse. The herbicidal evaluation was conducted on the 21 st day after treatment. The results were evaluated in accordance with the standards as identified in Table 5 and shown by the index numbers in Table 7.

As comparative agents, the same comparative compounds as disclosed in Test Example 1 were employed.

TABLE 7

| Compound No. | Herbicidal Effects | | | | |
|---|---|---|---|---|---|
| | Ec | Po | Am | Ch | Ci |
| 3 | 4 | 4 | 5 | 4 | 5 |
| 4 | 5 | 5 | 5 | 5 | 5 |
| 5 | 5 | 5 | 5 | 5 | 5 |
| 6 | 5 | 5 | 5 | 5 | 5 |
| 8 | 5 | 5 | 5 | 5 | 5 |
| 9 | 5 | 5 | 5 | 5 | 5 |
| 14 | 5 | 4 | 5 | 5 | 5 |
| 15 | 5 | 5 | 5 | 3 | 5 |
| 17 | 5 | 5 | 5 | 4 | 5 |
| 18 | 4 | 5 | 5 | 5 | 5 |
| 19 | 5 | 5 | 5 | 5 | 5 |
| 20 | 5 | 5 | 5 | 5 | 5 |
| 21 | 5 | 5 | 5 | 5 | 5 |
| 22 | 5 | 5 | 5 | 5 | 5 |
| 23 | 5 | 5 | 5 | 5 | 5 |
| 24 | 5 | 5 | 5 | 5 | 5 |
| 36 | 3 | 4 | 5 | 5 | 4 |
| 38 | 5 | 5 | 5 | 4 | 5 |
| 39 | 5 | 4 | 5 | 5 | 5 |
| 40 | 5 | 4 | 5 | 4 | 5 |
| 43 | 4 | 4 | 5 | 4 | 5 |
| 44 | 5 | 5 | 5 | 5 | 4 |
| 45 | 5 | 4 | 5 | 5 | 5 |
| 56 | 5 | 4 | 5 | 4 | 5 |
| 60 | 4 | 4 | 5 | 5 | 5 |
| 77 | 5 | 5 | 5 | 5 | 5 |
| 79 | 5 | 5 | 5 | 5 | 5 |
| 93 | 5 | 5 | 5 | 5 | 5 |

TABLE 7-continued

| Compound No. | Herbicidal Effects | | | | |
|---|---|---|---|---|---|
| | Ec | Po | Am | Ch | Ci |
| 94 | 4 | 5 | 5 | 5 | 5 |
| 95 | 5 | 5 | 5 | 5 | 5 |
| 96 | 5 | 5 | 5 | 5 | 5 |
| 97 | 5 | 5 | 5 | 5 | 5 |
| 104 | 5 | 5 | 5 | 5 | 5 |
| 106 | 4 | 5 | 5 | 5 | 5 |
| 116 | 5 | 4 | 4 | 5 | 5 |
| 120 | 5 | 5 | 5 | 5 | 5 |
| 121 | 5 | 5 | 5 | 5 | 5 |
| 122 | 5 | 5 | 5 | 5 | 5 |
| 132 | 4 | 4 | 5 | 5 | 5 |
| 139 | 5 | 5 | 5 | 5 | 5 |
| 140 | 5 | 4 | 5 | 5 | 5 |
| 141 | 5 | 5 | 5 | 5 | 5 |
| 142 | 5 | 5 | 5 | 5 | 5 |
| 145 | 5 | 5 | 5 | 5 | 5 |
| 146 | 5 | 5 | 5 | 5 | 5 |
| 147 | 4 | 4 | 5 | 5 | 5 |
| 148 | 5 | 5 | 4 | 4 | 5 |
| 149 | 4 | 4 | 5 | 5 | 5 |
| 151 | 5 | 5 | 5 | 5 | 5 |
| 152 | 5 | 4 | 5 | 5 | 5 |
| 153 | 4 | 5 | 5 | 5 | 5 |
| 156 | 5 | 5 | 5 | 5 | 5 |
| Comparative Example A | 0 | 0 | 4 | 1 | 0 |
| Comparative Example B | 0 | 0 | 0 | 0 | 0 |

Test Example 5:

Test on Herbicidal Effectiveness by Stem and Foliage Treatment

In a plastic pot (120 cm$^2$) filled with plowed field soil, seeds of barnyardgrass (abbreviated to as "Ec"), duckleaved (abbreviated to as "Po"), slender amaranth (abbreviated to as "Am"), common lambsquarters (abbreviated to as "Ch"), and rice flatsedge (abbreviated to as "Ci") were sown, and then grown in a greenhouse for 2 weeks. A wettable powder prepared in accordance with Formulation Example 2 was diluted with water and sprayed on the stems and foliages of the plant from the upper part of the plant to the whole thereof using a compact sprayer at a rate of 100 L of the wettable powder per 10 ares so that the ratio of the active ingredient was 400 g per 10 ares, followed by growing in a greenhouse. The herbicidal evaluation was conducted on the 14th day after treatment. The results were evaluated in accordance with the standards as identified in Table 5 and shown by the index numbers in Table 8.

As comparative agents, the same comparative compounds as disclosed in Test Example 1 were employed.

TABLE 8

| Compound No. | Herbicidal Effects | | | | |
|---|---|---|---|---|---|
| | Ec | Po | Am | Ch | Ci |
| 4 | 5 | 4 | 5 | 5 | 5 |
| 5 | 5 | 4 | 5 | 5 | 5 |
| 6 | 5 | 4 | 5 | 5 | 5 |
| 8 | 5 | 5 | 5 | 5 | 5 |
| 9 | 5 | 4 | 5 | 5 | 5 |
| 14 | 5 | 3 | 5 | 5 | 5 |
| 17 | 5 | 5 | 5 | 4 | 5 |
| 18 | 4 | 3 | 5 | 5 | 4 |
| 19 | 5 | 5 | 5 | 5 | 5 |
| 20 | 5 | 5 | 5 | 5 | 5 |
| 21 | 5 | 5 | 5 | 5 | 5 |
| 22 | 5 | 5 | 5 | 5 | 5 |

TABLE 8-continued

| Compound No. | Herbicidal Effects | | | | |
|---|---|---|---|---|---|
| | Ec | Po | Am | Ch | Ci |
| 23 | 5 | 5 | 5 | 5 | 5 |
| 24 | 5 | 5 | 5 | 5 | 5 |
| 38 | 4 | 4 | 5 | 4 | 3 |
| 39 | 4 | 5 | 5 | 4 | 4 |
| 40 | 4 | 4 | 5 | 4 | 4 |
| 44 | 5 | 4 | 5 | 5 | 5 |
| 45 | 5 | 5 | 5 | 5 | 5 |
| 52 | 5 | 5 | 5 | 5 | 5 |
| 56 | 5 | 5 | 5 | 5 | 5 |
| 60 | 5 | 5 | 5 | 5 | 5 |
| 77 | 5 | 5 | 5 | 5 | 5 |
| 79 | 4 | 5 | 5 | 5 | 5 |
| 81 | 5 | 5 | 5 | 5 | 5 |
| 93 | 5 | 5 | 5 | 5 | 5 |
| 94 | 5 | 5 | 5 | 5 | 5 |
| 95 | 5 | 5 | 5 | 5 | 5 |
| 96 | 5 | 5 | 5 | 5 | 5 |
| 97 | 5 | 5 | 5 | 5 | 5 |
| 104 | 5 | 5 | 5 | 5 | 5 |
| 106 | 3 | 5 | 5 | 5 | 4 |
| 116 | 5 | 4 | 5 | 4 | 5 |
| 118 | 5 | 5 | 5 | 5 | 5 |
| 120 | 5 | 5 | 5 | 5 | 5 |
| 121 | 5 | 5 | 5 | 5 | 5 |
| 122 | 4 | 5 | 5 | 5 | 5 |
| 139 | 5 | 5 | 5 | 5 | 5 |
| 140 | 5 | 5 | 5 | 5 | 5 |
| 141 | 5 | 5 | 5 | 5 | 5 |
| 142 | 5 | 5 | 5 | 5 | 5 |
| 145 | 5 | 5 | 5 | 5 | 5 |
| 146 | 5 | 5 | 5 | 5 | 5 |
| 147 | 5 | 5 | 5 | 5 | 5 |
| 148 | 5 | 5 | 5 | 5 | 5 |
| 149 | 4 | 5 | 5 | 5 | 5 |
| 150 | 5 | 5 | 5 | 5 | 5 |
| 151 | 5 | 5 | 5 | 5 | 5 |
| 152 | 5 | 4 | 5 | 5 | 4 |
| 153 | 5 | 5 | 5 | 5 | 5 |
| 156 | 5 | 5 | 5 | 5 | 5 |
| Comparative Example A | 0 | 0 | 4 | 2 | 4 |
| Comparative Example B | 0 | 0 | 4 | 3 | 4 |

Test Example 6:

Test of Plant Selectivity by Plowed Field Soil Treatment

In a plastic pot (600 cm$^2$) filled with plowed field soil, seeds of soybean (abbreviated to as "Gl"), blue morning-glory (abbreviated to as "Ip"), and common cucklebur (abbreviated to as "Xa") were sown, and covered with soil. The next day, a predetermined effective amount (ai, g/10a) of a wettable powder prepared in accordance with Formulation Example 1 was diluted with water and sprayed uniformly on the plowed field soil using a compact sprayer at a rate of 100 L of the wettable powder per 10 ares, followed by growing in a greenhouse. The herbicidal evaluation was conducted on the 21st day after treatment. The results were evaluated in accordance with the standards as identified in Table 5 and shown by the index numbers in Table 9.

TABLE 9

| Compound No. | Dose of active ingredient ai, g/10 a | Herbicidal Effects | | Phytotoxicity |
|---|---|---|---|---|
| | | Ip | Xa | Gl |
| 18 | 25 | 5 | 5 | 0 |
| 19 | 6.3 | 5 | 5 | 0 |

TABLE 9-continued

| Compound No. | Dose of active ingredient ai, g/10 a | Herbicidal Effects | | Phytotoxicity |
|---|---|---|---|---|
| | | Ip | Xa | Gl |
| 20 | 6.3 | 5 | 5 | 0 |
| 22 | 6.3 | 5 | 5 | 0 |
| 93 | 1.6 | 4 | 5 | 0 |
| 96 | 1.6 | 4 | 5 | 0 |
| 97 | 6.3 | 5 | 5 | 0 |
| 145 | 6.3 | 5 | 5 | 0 |
| 156 | 25 | 5 | 5 | 0 |

Test Example 7:

Test of Plant Selectivity by Stem and Foliage Treatment

In a plastic pot (600 cm$^2$) filled with plowed field soil, seeds of soybean (abbreviated to as "Gl"), blue morning-glory (abbreviated to as "Ip"), and common cucklebur (abbreviated to as "Xa") were sown, and covered with soil, followed by growing in a greenhouse for 2 weeks. A predetermined effective amount (ai, g/10a) of a wettable powder prepared in accordance with Formulation Example 1 was diluted with water and sprayed uniformly on the stems and foliages of the plants from the upper pan of the plant to the whole thereof using a compact sprayer at a rate of 100 L of the wettable powder per 10 ares, followed by growing in a greenhouse. The herbicidal evaluation was conducted on the 14th day after treatment. The results were evaluated in accordance with the standards as identified in Table 5 and shown by the index numbers in Table 10.

TABLE 10

| Compound No. | Dose of active ingredient ai, g/10 a | Herbicidal Effects | | Phytotoxicity |
|---|---|---|---|---|
| | | Ip | Xa | Gl |
| 20 | 6.3 | 5 | 5 | 0 |
| 22 | 6.3 | 5 | 5 | 1 |
| 97 | 1.6 | 5 | 5 | 1 |
| 104 | 1.6 | 4 | 5 | 1 |
| 145 | 6.3 | 5 | 5 | 0 |
| 156 | 1.6 | 5 | 5 | 0 |

What is claimed is:

1. A compound of the formula:

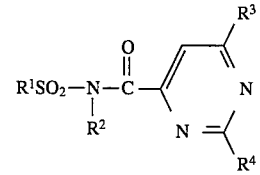

wherein R$^1$ represents a) a C$_{1-10}$ alkyl group {optionally having mono-substituent or poly-substituents selected from the group consisting of a halogen atom, a C$_{3-8}$ cycloalkyl group, an R$^7$O- group (wherein R$^7$ represents a hydrogen atom, a C$_{1-10}$ alkyl group, a C$_{2-8}$ alkenyl group, a C$_{2-8}$ alkynyl group, a phenyl group (optionally having mono-substituent or poly-substituents selected from the group consisting of a halogen atom, a C$_{1-10}$ alkyl group, a C$_{1-6}$ alkoxy group, a C$_{1-10}$ haloalkyl group, and a C$_{1-6}$ alkoxycarbonyl group)), an R$^7$S(O)$_n$- group (wherein R$^7$ has the same meaning as defined above, n is an integer from 0 to 2), an $R^7R^8N$- group (wherein $R^7$ has the same meaning as defined above, $R^8$ represents a $C_{1-10}$ alkyl group, a $C_{2-8}$ alkenyl group, a $C_{2-8}$ alkynyl group, a $C_{1-6}$ alkoxy group, a $C_{2-8}$ alkenyloxy group, $C_{2-8}$ alkynyloxy group, or a phenyl group (optionally having monosubstituent or poly-substituents selected from the group consisting of a halogen atom, a $C_{1-10}$ alkyl group, a $C_{1-6}$ alkoxy group, a $C_{1-10}$ haloalkyl group, and a $C_{1-6}$ alkoxycarbonyl group)), a trimethylsilyl group, a cyano group, a $C_2$ oxiranyl group, an $R^8CO$- group (wherein $R^8$ has the same meaning as defined above) and an

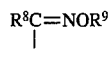

group (wherein $R^8$ has the same meaning as defined above, and $R^9$ represents a $C_{1-10}$ alkyl group, a $C_{2-8}$ alkenyl group, or a $C_{2-8}$ alkynyl group)}, b) a $C_{2-8}$ alkenyl group {optionally having mono-substituent or poly-substituents selected from the group consisting of a halogen atom, a phenyl group (optionally having mono-substituent or poly-substituents selected from the group consisting of a halogen atom, a $C_{1-10}$ alkyl group, a $C_{1-6}$ alkoxy group, a $C_{1-10}$ haloalkyl group, and a $C_{1-6}$ alkoxycarbonyl group), a $C_{3-8}$ cycloalkyl group, an $R^7O$- group (wherein $R^7$ has the same meaning as defined above), an $R^7S(O)_n$- group (wherein $R^7$ and n have the same meanings as defined above), an $R^7R^8N$- group (wherein $R^7$ and $R^8$ have the same meaning as defined above), a trimethylsilyl group, a cyano group, an $R^8CO$- group (wherein $R^8$ has the same meaning as defined above), and an

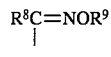

group (wherein $R^8$ and $R^9$ have the same meanings as defined above)}, c) a $C_{2-8}$ alkynyl group, d) a $C_{3-8}$ cycloalkyl group { optionally having mono-substituent or poly-substituents selected from the group consisting of a halogen atom, a $C_{1-10}$ alkyl group, a phenyl group (optionally having mono-substituent or poly-substituents selected from the group consisting of a halogen atom, a $C_{1-10}$ alkyl group, a $C_{1-6}$ alkoxy group, a $C_{1-10}$ haloalkyl group, and a $C_{1-6}$ alkoxycarbonyl group), an $R^7O$- group (wherein $R^7$ has the same meaning as defined above), an $R^7S(O)n$- group (wherein $R^7$ and n have the same meaning as defined above), an $R^7R^8N$- group (wherein $R^7$ and $R^8$ have the same meaning as defined above), a trimethylsilyl group, a cyano group, an oxo group, a $=NOR^9$ group (wherein $R^9$ has the same meaning as defined above), an $R^8CO$- group (wherein $R^8$ has the same meaning as defined above), and an

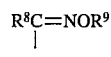

group (wherein $R^8$ and $R^9$ have the same meanings as defined above)}, e) a $C_{3-8}$ cycloalkenyl group {optionally having mono-substituent or poly-substituents selected from the group consisting of a halogen atom, a $C_{1-10}$ alkyl group, a phenyl group (optionally having mono-substituent or poly-substituents selected from the group consisting of a halogen atom, an $C_{1-10}$ alkyl group, a $C_{1-6}$ alkoxy group, a $C_{1-10}$ haloalkyl group, and a $C_{1-6}$ alkoxycarbonyl group), an $R^7O$- group (wherein $R^7$ has the same meaning as defined above), an $R^7S(O)_n$- group (wherein $R^7$ and n have the same meanings as defined above), an $R^7R^8N$- group (wherein $R^7$ and $R^8$ have the same meanings as defined above), a trimethylsilyl group, a cyano group, an oxo group, a $=NOR^9$ group (wherein $R^9$ has the same meaning as defined above), an $R^8CO$- group (wherein $R^8$ has the same meaning as defined above), and an $R^8C=NOR^9$ group (wherein $R^8$ and $R^9$ have the same meanings as defined above)}, f) an $R^5R^6N$- group wherein $R^5$ represents i) a $C_{1-10}$ alkyl group {optionally having mono-substituent or poly-substituents selected from the group consisting of a halogen atom, a $C_{3-8}$ cycloalkyl group, an $R^7O$ group (wherein $R^7$ has the same meaning as defined above), an $R^7S(O)_n$- group (wherein $R^7$ and n have the same meanings as defined above), an $R^7R^8N$- group (wherein $R^7$ and $R^8$ have the same meaning as defined above), a trimethylsilyl group, a cyano group, an oxiranyl group, an $R^8CO$- group (wherein $R^8$ has the same meaning as defined above) and an

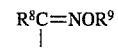

group (wherein $R^8$ and $R^9$ have the same meanings as defined above)}, ii) a $C_{2-8}$ alkenyl group {optionally having mono-substituent or poly-substituents selected from the group consisting of a halogen atom, a phenyl group (optionally having mono-substituent or poly-substituents selected from the group consisting of a halogen atom, a $C_{1-10}$ alkyl group, an $C_{1-6}$ alkoxy group, a $C_{1-10}$ haloalkyl group, and a $C_{1-6}$ alkoxycarbonyl group), a $C_{3-8}$ cycloalkyl group, an $R^7O$- group (wherein $R^7$ has the same meaning as defined above), an $R^7S(O)_n$- group (wherein $R^7$ and n have the same meanings as defined above), an $R^7R^8N$- group (wherein $R^7$ and $R^8$ have the same meanings as defined above), a trimethylsilyl group, a cyano group, an $R^8CO$- group (wherein $R^8$ has the same meaning as defined above), and an

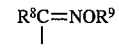

group (wherein $R^8$ and $R^9$ have the same meanings as defined above)}, iii) a $C_{2-8}$ alkynyl group, iv) a $C_{3-8}$ cycloalkyl group {optionally having mono-substituent or poly-substituents selected from the group consisting of a halogen atom, a $C_{1-10}$ alkyl group, a phenyl group (optionally having mono-substituent or poly-substituents selected from the group consisting of a halogen atom, a $C_{1-10}$ alkyl group, a $C_{1-6}$ alkoxy group, a $C_{1-10}$ haloalkyl group, and a $C_{1-6}$ alkoxycarbonyl group), an $R^7O$- group (wherein $R^7$ has the same meaning as defined above), an $R^7S(O)_n$- group (wherein $R^7$ and n have the same meanings as defined above), an $R^7R^8N$- group (wherein $R^7$ and $R^8$ have the same meanings as defined above), a trimethylsilyl group, a cyano group, an oxo group, a $=NOR^9$ group (wherein $R^9$ has the same meaning as defined above), an R⁸CO -group (wherein R⁸ has the same meaning as defined above), and an

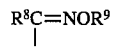

group (wherein R⁸ and R⁹ have the same meanings as defined above)}, v) a $C_{3-8}$ cycloalkenyl group {optionally having mono-substituent or poly-substituents selected from the group consisting of a halogen atom, a $C_{1-10}$ alkyl group, a phenyl group (optionally having mono-substituent or poly-substituents selected from the group consisting of a halogen atom, a $C_{1-10}$ alkyl group, a $C_{1-6}$ alkoxy group, a $C_{1-10}$ haloalkyl group, and a $C_{1-6}$ alkoxycarbonyl group), an R⁷O- group (wherein R⁷ has the same meaning as defined above), an R⁷S(O)$_n$- group (wherein R⁷ and n have the same meanings as defined above), an R⁷R⁸N- group (wherein R⁷ and R⁸ have the same meanings as defined above), a trimethylsilyl group, a cyano group, an oxo group, a =NOR⁹ group (wherein R⁹ has the same meaning as defined above), an R⁸CO- group (wherein R⁸ has the same meaning as defined above), and an

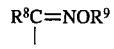

group (wherein R⁸ and R⁹ have the same meanings as defined above)}, vi) an R⁷O- group (wherein R⁷ has the same meaning as defined above), and R⁶ represents a hydrogen atom or R⁵, R⁵ and R⁶ may be independent of each other, or R⁵ may form a 3-member to 8-member ring with R⁶ and the nitrogen atom, g) an

group (wherein R⁶ has the same meaning as defined above), and R¹⁰ represents i) a $C_{1-10}$ alkyl group {optionally having mono-substituent or poly-substituents selected from the group consisting of a halogen atom, an R⁷O- group (wherein R⁷ has the same meaning as defined above), an R⁷S(O)$_n$- group (wherein R⁷ and n have the same meanings as defined above), an R⁷R⁸N- group (wherein R⁷ and R⁸ have the same meanings as defined above), and a cyano group}, ii) a $C_{2-8}$ alkenyl group {optionally having mono-substituent or poly-substituents selected from the group consisting of a halogen atom, an R⁷O- group (wherein R⁷ has the same meaning as defined above), an R⁷S(O)$_n$- group (wherein R⁷ and n have the same meanings as defined above), an R⁷R⁸N- group (wherein R⁷ and R⁸ have the same meanings as defined above), and a cyano group}, iii) a phenyl group {optionally having mono-substituent or poly-substituents selected from the group consisting of a halogen atom, a $C_{1-10}$ alkyl group, a $C_{1-6}$ alkoxy group, a $C_{1-10}$ haloalkyl group, and a $C_{1-6}$ alkoxycarbonyl group}, or h) an

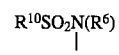

group (wherein R⁶ and R¹⁰ have the same meanings as defined above);

R² represents a hydrogen atom or a $C_{1-10}$ alkyl group (optionally having a substituent selected from the group consisting of a $C_{1-6}$ alkoxy group and a $C_{1-6}$ alkoxycarbonyl group), a benzyl group, or a $C_{2-8}$ alkenyl group;

R³ and R⁴ represent independently a hydrogen atom, a halogen atom, a $C_{1-10}$ alkyl group, an R⁷O- group (wherein R⁷ has the same meaning as defined above), an R⁷S(O)$_n$- group (wherein R⁷ and n have the same meanings as defined above), an R⁷R⁸N- group (wherein R⁷ and R⁸ have the same meanings as defined above), a $C_{1-10}$ haloalkyl group, or a $C_{1-6}$ haloalkoxy group; or salt thereof.

2. A compound of the formula:

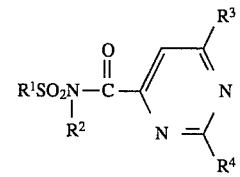

wherein R¹ represents a) a $C_{1-10}$ alkyl group {optionally having mono-substituent or poly-substituents selected from the group consisting of a halogen atom, a $C_{3-8}$ cycloalkyl group, an R⁷O- group (wherein R⁷ represents a hydrogen atom, a $C_{1-10}$ alkyl group, a phenyl group (optionally having substituent selected from the group consisting of a halogen atom, a $C_{1-10}$ alkyl group)), an R⁷S(O)$_n$- group (wherein R⁷ has the same meaning as defined above, n is an integer from 0 to 2), a trimethylsilyl group, a cyano group, an oxiranyl group, an R⁸CO- group (wherein R⁸ represents a $C_{1-10}$ alkyl group, a phenyl group, or a $C_{1-6}$ alkoxy group), and an

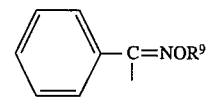

group (wherein R⁹ represents a $C_{1-10}$ alkyl group)}, b) a $C_{2-8}$ alkenyl group {optionally having mono-substituent or poly-substituents selected from the group consisting of a halogen atom, a phenyl group, an R⁷S(O)$_n$- group (wherein R⁷ and n have the same meanings as defined above), and an R⁸CO group (wherein R⁸ has the same meaning as defined above)}, c) a $C_{2-8}$ alkynyl group, d) a $C_{3-8}$ cycloalkyl group {optionally having a substituent selected from the group consisting of an oxo group)}, e) an R⁵R⁶N- group wherein R⁵ represents i) a $C_{1-10}$ alkyl group {optionally having mono-substituent or poly-substituents selected from the group consisting of a halogen atom, an R⁷O- group (wherein R⁷ has the same meaning as defined above), and an R⁸CO- group (wherein R⁸ has the same meaning as defined above)}, ii) a $C_{2-8}$ alkenyl group {optionally being substituted with a halogen atom},
iii) a $C_{2-8}$ alkynyl group,
iv) a $C_{3-8}$ cycloalkyl group, and
v) a $C_{1-6}$ alkoxy group, and $R^6$ represents a hydrogen atom or $R^5$ ($R^5$ and $R^6$ may be independent of each other), or $R^5$ may form a 3-member to 8-member ring with $R^6$ and the nitrogen atom, f) an

group {wherein $R^{10}$ represents a phenyl group (optionally being substituted with a halogen atom)}, or g) an

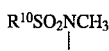

group (wherein $R^6$ and $R^{10}$ have the same meanings as defined above);

$R^2$ represents a hydrogen atom or a $C_{1-10}$ alkyl group (optionally having a substituent selected from the group consisting of a $C_{1-6}$ alkoxy group and a $C_{1-6}$ alkoxycarbonyl group), a benzyl group, or a $C_{2-8}$ alkenyl group;

$R^3$ and $R^4$ represent independently a halogen atom, a $C_{1-10}$ alkyl group, a $C_{1-6}$ alkoxy group, a phenoxy group (optionally substituted with a methyl group), a dimethylamino group; or salt thereof.

3. A compound of the formula:

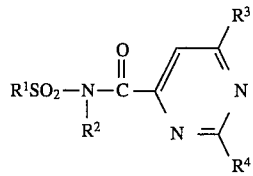

wherein $R^1$ represents a) a $C_{1-10}$ alkyl group {optionally having mono-substituent or poly-substituents selected from the group consisting of a halogen atom, a $C_{3-8}$ cycloalkyl group, an $R^7O$- group (wherein $R^7$ represents a $C_{1-10}$ alkyl group), an $R^7S(O)_n$- group (wherein $R^7$ has the same meaning as defined above, n is an integer from 0 to 1), an oxiranyl group and an $R^8CO$- group wherein $R^8$ represents a $C_{1-6}$ alkoxy group)}, b) a $C_{2-8}$ alkenyl group (optionally having mono-substituent or poly-substituents selected from the group consisting of halogen atoms), c) a $C_{2-8}$ alkynyl group, d) a $C_{3-8}$ cycloalkyl group, e) an $R^5R^6N$- group wherein $R^5$ represents
  i) a $C_{1-10}$ alkyl group {optionally having mono-substituent or poly-substituents selected from the group consisting of an $R^7O$- group (wherein $R^7$ has the same meaning as defined above)},
  ii) a $C_{2-8}$ alkenyl group
  iii) a $C_{3-8}$ alkynyl group
  iv) a $C_{3-8}$ cycloalkyl group, and
  v) a $C_{1-6}$ alkoxy group, and $R^6$ represents a hydrogen atom or has the same meaning as $R^5$ ($R^5$ and $R^6$ are independent of each other);

$R^2$ represents a hydrogen atom or a $C_{1-10}$ alkyl group (optionally having a substituent selected from the group consisting of a $C_{1-6}$ alkoxy group);

$R^3$ and $R^4$ represent independently a halogen atom, a $C_{1-10}$ alkyl group, an $R^7O$- group (wherein $R^7$ has the same meaning as defined above), or an $R^7R^7N$- group (wherein $R^7$ has the same meaning as defined above); or salt thereof.

* * * * *